(12) United States Patent
Davis, Jr.

(10) Patent No.: US 10,166,361 B2
(45) Date of Patent: *Jan. 1, 2019

(54) METHOD AND APPARATUS FOR AMBIENT SOUND THERAPY USER INTERFACE AND CONTROL SYSTEM

(71) Applicant: Louis Fisher Davis, Jr., Omaha, NE (US)

(72) Inventor: Louis Fisher Davis, Jr., Omaha, NE (US)

( * ) Notice: Subject to any disclaimer, the term of this patent is extended or adjusted under 35 U.S.C. 154(b) by 408 days.

This patent is subject to a terminal disclaimer.

(21) Appl. No.: 14/158,244

(22) Filed: Jan. 17, 2014

(65) Prior Publication Data

US 2014/0163311 A1    Jun. 12, 2014

Related U.S. Application Data

(62) Division of application No. 11/163,179, filed on Oct. 7, 2005, now Pat. No. 8,634,572.
(Continued)

(51) Int. Cl.
| | |
|---|---|
| *A61M 21/02* | (2006.01) |
| *H04R 5/027* | (2006.01) |
| *H04S 3/00* | (2006.01) |
| *H04R 1/40* | (2006.01) |
| *H04R 3/12* | (2006.01) |
| *A61M 21/00* | (2006.01) |

(52) U.S. Cl.
CPC .............. *A61M 21/02* (2013.01); *H04R 1/406* (2013.01); *H04R 3/12* (2013.01); *H04R 5/027* (2013.01); *H04S 3/002* (2013.01); *A61M 2021/0027* (2013.01); *H04R 2201/401* (2013.01)

(58) Field of Classification Search
CPC .......... H04R 3/005; H04R 3/12; H04R 1/406; H04R 5/027; H04R 2201/401; H04S 3/00; H04S 3/002; A61M 2021/0027; A61M 21/02
USPC ......... 381/124, 56, 57, 92, 80, 301, 368, 77, 381/122; 704/503, 504
See application file for complete search history.

(56) References Cited

U.S. PATENT DOCUMENTS

| | | |
|---|---|---|
| 3,651,286 A | 3/1972 | Gorike et al. |
| 3,710,034 A | 1/1973 | Murry |
| | (Continued) | |

FOREIGN PATENT DOCUMENTS

| | | | |
|---|---|---|---|
| EP | 0848572 A1 * | 6/1998 | ............. H04R 5/027 |
| JP | 53-58201 | 5/1978 | |
| | (Continued) | | |

OTHER PUBLICATIONS

Cool Edit User's Manual, 1996.
(Continued)

*Primary Examiner* — Vivian C Chin
*Assistant Examiner* — Douglas J Suthers
(74) *Attorney, Agent, or Firm* — Mark E. Stallion; Greensfelder, Hemker & Gale, P.C.

(57) ABSTRACT

Method and apparatus comprising a method of recording natural sounds with a matched microphone array, recording the signal on a high resolution recording device including creating an audio bed, and playing back the recording on a tuned playback system. The method and apparatus is used to create or duplicate an ambient sound space for ambient therapy.

9 Claims, 7 Drawing Sheets

Related U.S. Application Data

(60) Provisional application No. 60/643,468, filed on Jan. 13, 2005, provisional application No. 60/595,408, filed on Jun. 30, 2005.

(56) References Cited

U.S. PATENT DOCUMENTS

| | | | |
|---|---|---|---|
| 4,038,499 | A | 7/1977 | Yeaple |
| 4,082,918 | A | 4/1978 | Chang et al. |
| 4,194,096 | A | 3/1980 | Ramsey |
| 4,480,146 | A | 10/1984 | Invernizzi |
| 5,058,170 | A | 10/1991 | Kanamori et al. |
| 5,219,322 | A | 6/1993 | Weathers |
| 5,239,587 | A | 8/1993 | Muckelrath |
| 5,260,920 | A * | 11/1993 | Ide .......................... G09B 9/22 369/5 |
| 5,304,112 | A | 4/1994 | Mrklas et al. |
| 5,778,083 | A | 7/1998 | Godfrey |
| 6,072,878 | A | 6/2000 | Moorer |
| 6,254,527 | B1 | 7/2001 | August |
| 6,366,679 | B1 | 4/2002 | Steffen et al. |
| 6,484,062 | B1 | 11/2002 | Kim |
| 6,535,610 | B1 | 3/2003 | Stewart |
| 6,608,903 | B1 | 8/2003 | Miyazaki et al. |
| RE38,350 | E | 12/2003 | Godfrey |
| 6,782,104 | B1 | 8/2004 | Vieilledent |
| 6,845,163 | B1 | 1/2005 | Johnston et al. |
| 2003/0138106 | A1 | 7/2003 | Dabringhaus |
| 2003/0185404 | A1* | 10/2003 | Milsap .................... H04R 3/12 381/77 |

FOREIGN PATENT DOCUMENTS

| | | |
|---|---|---|
| JP | 60-156699 | 10/1985 |
| JP | 08-130787 | 5/1996 |
| JP | 10-507892 | 7/1998 |
| JP | 10-304484 | 11/1998 |
| JP | 11-262097 | 9/1999 |
| JP | 2000-341783 | 8/2000 |
| JP | 2002-345064 | 11/2002 |
| KR | 1993-0001076 B1 | 2/1993 |

OTHER PUBLICATIONS

The NASA STI Program Office; "3-D Sound for Virtual Reality and Multimedia;" Pub. Apr. 2000; Introduction/Acknowledgements 4 pages, Table of Contents 8 pages, and Publication 234 pages; National Aeronautics and Space Administration, Ames Research Center, Moffett Field, California.

* cited by examiner

METHOD AND APPARATUS FOR AMBIENT SOUND THERAPY USER INTERFACE AND CONTROL SYSTEM

CROSS-REFERENCE TO RELATED APPLICATIONS

This application is a divisional application of U.S. patent application Ser. No. 11/163,179, filed Oct. 7, 2005, which claims priority to and the benefit of U.S. Provisional App. Ser. No. 60/595,408 filed Jun. 30, 2005 and U.S. Provisional App. Ser. No. 60/643,468 filed Jan. 13, 2005, the entire contents of all of which are incorporated herein by reference.

BACKGROUND OF INVENTION

Field of Invention

This invention relates generally to a method and apparatus using ambient sounds for a therapeutic effect and, more particularly, to a method and apparatus for duplicating an ambient sound space.

Background Art

There are various audio recording methods and apparatus and audio playback systems that are intended to mimic the acoustics of a given space in a space different from the given space for which the acoustics are being mimicked with a recording and playback system. For example, the acoustic experience when listening to a full orchestra in an open amphitheatre is different than listening to the same orchestra in a concert hall, which is again different than listening to the same orchestra in a large convention hall or a recording studio.

The acoustics of each venue is different due to the dimensions, material of surrounding structures and etc. . . . The acoustic differences are due to the different sound reflections and absorptions and etc. . . . Therefore, the sounds emanating from the orchestra will have a different sound quality and fidelity to the listener depending on the acoustics of the venue. If the sounds emanating from an orchestra playing in any venue are recorded and played back with the standard recording and play back system, then the music sounds as received by the listener upon playback does not mimic the acoustics of the venue. In other words, the acoustic experience of the listener during playback does not mimic the acoustic experience of a live performance being heard by the listener in the original venue.

Some listeners may prefer to hear a rock band in an amphitheatre venue and hear a full orchestra in a concert hall. Methods and systems for recording and playback have been designed to give listeners that choice when listening to recorded music on a playback system that simulates the acoustical dynamics of a given type of venue. Some recording and playback methods have attempted to simulate the acoustics of famous venues like Carnegie Hall.

There are also various recording methods and systems for using various musical tracks sometimes combined with natural or simulated sounds, such as ocean waves, to induce a therapeutic or calming effect. However, neither of the above methods or systems provides for duplicating and/or enhancing a given ambient sound space and playing back in a different play back sound space for inducing a therapeutic result.

BRIEF SUMMARY OF INVENTION

The invention is a method and apparatus for recording and playing back of natural and/or enhanced natural sounds to capture and reproduce and ambient sound space in a different sound space in such a manner to cause a therapeutic effect. The method and apparatus comprises a method of recording natural sounds with a matched microphone array, recording the signal on a high resolution recording device including creating an audio bed, and playing back the recording on a playback system tuned for the play back space such that the playback experience mimics the original sound space. The method and apparatus is used to create or duplicate an ambient sound space for ambient therapy in order to give a patient a feeling they are actually in the original ambient sound recorded space.

The present ambient therapy invention comprises a combination of natural sounds, which in one embodiment can be for example recorded in a 200'×200' algorithm, in combination with musical parts that spring from sound events in the natural sounds to address or induce a certain emotional therapeutic effect. The invention embodies the concept of Psychoacoustics, which suggests that an individual believes they are where their ears tell them they are. There are various elements key to this method of putting the patient and those attending to the patient at ease by distracting them with a believable phenomenon including a noise floor, a time shift and distance algorithm/spatial perception.

There is typically a certain amount of ambient noise surrounding us in most of our everyday world. However, from time to time, there are abrupt high transient spikes in the normal pattern of sounds around us that disrupt us, which are sometimes referred to as startle sounds. The drone of consistency can give an individual the comfort of a sense of well being. The present invention is a method of producing a drone of natural sounds with systematic overlays that will mask transient noise that is novel over typical sound masking techniques.

Typical surround playback systems are comprised of a set of five satellite speakers with a sub woofer and a playback unit which powers the speakers and reads the DVD media. These type systems have proven fairly simple and can allow one the ability to quickly illustrate the program material of the present invention. In these demonstrations it becomes clear that the home theater systems could be improved upon in a project that would encompass the complete idea of the ambient therapy system. The concept is not a home entertainment system nor a standard surround recording and playback system nor a scheme or digital signal processing system for replicating the acoustics of a particular venue.

The standard surround sound system includes front right, left and center channels; left and right rear channels and a subwoofer. The three front channels provide the primary portion of the portions of the sound dynamic and the three front playback speakers are typically positioned forward of the listener. The sub-woofer is typically dedicated to the lower frequency sounds and the speaker in the playback system is usually centrally positioned within the playback area or room. The left and right rear channels usually provide the secondary portion of the sound dynamic to provide the sound reflection and delay effect and these speakers are usually positioned rearward of the listener.

Whereas, the present invention creates a media playback system that focuses on ambient therapy fundamentals and embodies the concept by providing a novel recording and playback method. The ambient sounds are captured by four independent multidirectional microphones connected on four separate recording channels and arranged in a 200'×200' recording array. The four channel playback system will play back the four independently recorded channels on four corresponding play back channels and speakers. The built in sound delays created by the independent multidirectional microphones arranged in a 200'×200' recording array and other sound dynamics are replicated on the four playback channels in order to replicate the sound space of the 200'×200' recording area. The sound or time delay realized by the independent microphones during recording is matched and replicated by the playback channels and speakers. The play back system can also, optionally include a subwoofer channel. The Ambient Therapy System (ATS) and its components can function in a hospital recovery room and therapeutic environment. The present invention however is the method of recording and playing back and is not specifically related to the electronic components used to implement the method. The dimensions of the recording array may vary to create and optional sound space.

The present invention provides a device to eliminate the fact that the user is operating a machine, but rather, creates a world or sound space of audible ambience far removed from the noises and beeps generated by all the medical related machinery which plague the recovery room in a typical hospital. The playback system can be designed to be very transparent and can allow the patient to not focus on the fact they are listening to an audio recording and convince them they were somewhere other than a hospital room, in pain, and recovering from or preparing to enter surgery. Therefore, one goal is to have equipment that is physically discrete, and where there is Low visual impact of equipment, concealed and unobtrusive.

The present system provides a user interface that is simple to operate and is not visually distracting or obtrusive. Along with the playback equipment, the speakers that are the sound sources for the ambient programs and are concealed, further allowing the patient to feel that they aren't listening to speakers, but instead feeling as though they are actually in the original recorded environment of sound space of the program being played back. Along with being visually concealed, the present invention has minimum controls to allow the maximum amount of user control necessary to playback the ambient sound material.

The system provides a pertinent and effective user interface. The user interface comprises a set of input controls that correspond exactly to the functions needed as well as a simple and easy to understand indication and display section for selecting the desired program to be played and the style i.e. ambience or music only or both, by which the program is played back. The playback system can include a touch screen monitor user interface for selecting the various modes of operation as well as programming the play back function. The playback system can be designed to be able to receive new programming when it is available. For example, the ATS playback system can be designed such that it includes a removable module that can be returned to the provider of the ATS for upgrading. Alternatively the ATS playback system can include a swappable hard drive that can be removed and replaced with a hard drive containing new programming. The ATS playback system can also have a communication link for upgrading by uploading new programs via a network interface, such as for example a Wide Area Network (WAN) such as the internet.

One embodiment of the playback system architecture includes a Speaker System that can be designed to match and replicate the recording array. In order to meet the above criteria for concealment of the speakers, it is desirable to utilize a suitable device to playback at a fidelity meeting or exceeding desired requirements for the audio as well as to utilize a speaker that can be almost hidden when installed. One embodiment comprises a ceiling mount speaker scenario that mounts flush into a suspended ceiling tile. The speakers themselves can comprise a magnetically shielded aluminum cone driver and a back can be utilized, which insulates and provides the proper cabinet size to maximize the speaker's characteristics. It also allows for a much easier installation and smoother integration into existing hospital rooms which can't be freed up for long periods of time for the installation process. Unlike traditional ceiling mount commercial speakers systems, the ones utilized in the present invention can be low voltage instead of the industry standard 70V speakers which require step up and step down impedance matching transformers to operate. With these particular type of speakers, they have a dispersion pattern for a fairly large coverage area which allows for making the choice of speaker placement a little easier.

The speakers can be statically mounted, which doesn't allow for physically moving them as would a wall mount type of speaker with ball and cup mount, but again, the coverage area is such that being able to adjust the sound field for a patient's bed area in a hospital room won't be difficult. It will simply be a matter of locating the speakers in the appropriate ceiling tiles and adjusting the volume on the individual speaker channels to balance the program where a patient's head may be laying in the bed. Another aspect of the ceiling mount type of speaker is its inherent adherence to typical building plenum space fire codes. When used with the appropriate plenum rated speaker wiring, these speakers easily exceed any fire codes that may exist. The speaker, however, can be mounted in any other appropriate area or can be integrated with various furnishings such as beds or end tables within a hospital room.

The drivers for the speakers are full range devices, which allow for very high fidelity audio without need for added filtering and such to compensate for inefficiencies in traditional designs. With a single driver of this nature, the cost of the speaker array is greatly reduced due to the lower parts count. In using a full range device, one possible embodiment of the invention comprises reducing the number of speakers in the surround array to just four instead of five with a subwoofer. This scenario may prove even more attractive for the prospective hospital clients that may be reluctant to install an audio system with a subwoofer. The main goal of the speaker array is to convey the spatial relationships and delays present in the original surround recording space. One focus is to maintain high quality audio fidelity and the surround image that is its fingerprint.

The ATS playback box can be built upon essentially a small PC motherboard. The unit can contain a hard drive which will hold the ambient programs. There can also be an audio sound board to which the computer sends the program data and then it's converted to the audible analog ambient program. Included inside the main chassis of the box there can be the motherboard, the audio board, the hard drive, the user interface, the power distribution section and the audio power amplifier section to drive the speakers. The main power to the box can be supplied by an external power supply that plugs into regular line power from a standard 110V wall outlet and transforms the power down to the level needed by the box itself. The unit can be designed to be low power and extremely quiet, which lends itself to the concealment and low profile criteria for the ambient therapy system. This size can be minimized to make it easy to conceal and adapt to the hospital décor.

By constructing the ATS on the infrastructure of the computer system, there is the ability to augment the design in the future to improve upon the features that the unit can contain. The computer system being utilized can also contain a built in network interface. With this interface in place, there is an ability to build in provisions for upgrading program material through the internet or other wide area network. This will make the unit very flexible and eases the responsibility of the end user of having to maintain upgrades.

The computer also serves as a liaison to the user by providing the information on the program being played and the method by which it's played via the display section in the user interface. Encompassed in the user interface are the input controls for the user to select the program, adjust the volume, etc. For the ATS's box, the complexity of a typical home theater system's user interface can be avoided. One goal is to keep it as simple as possible and clearly define the functions for the user so there is minimal ambiguity.

Within the ATS's case, a small but efficient power amplifier can be housed to handle the driving of the speakers in the surround array. The amplifiers are tailored specific for the speakers they are driving. This allows us to shape the tonal characteristics imparted by the speaker to allow for a more transparent sound source as if the speaker system weren't actually there. The amplifier can provide for an equalization or tonality adjustment of the output signal driving the speakers to compensate for inaccuracies in sound reproduction. For example, providing an equalization adjustment operable to flatten out the speaker output for more accurate reproduction of the recorded sound. It can be an equalization adjustment at the time of mixing and/or designed into an ATS box adjusted for a specific set of speakers.

The recording algorithm for recording the nature sounds is also a key aspect of the invention, which is designed to be weatherproof and somewhat animal proof. The height for the microphone assembles can be about approximately 30" when they are inserted into the ground. This puts the microphone position at a little more than about approximately two feet above the ground. The height can vary depending on the recording environment and the desired result. The top of the microphone cage can be semi-spherical which aids in allowing water to run off and down the sides instead of dripping into the microphone area. The legs of the cage can be made from 302 stainless steel so that they can be inserted into the ground with little or no corrosion. The windscreens can be a nylon material much like the material used in the Rycote type microphones. A number of other materials that would dampen the wind noise and at the same time would be somewhat weather resistant could be utilized to obtain a similar result. The invention comprises a feature to combat the mouse/rodent problem that may occur. A braided wire mesh cage covers the microphone cabling from the external connector on up to and covering the microphone. The microphone that can be used internal to the cage is a DPA miniature condensor microphone. A Shure microphone product which is less expensive can also be used.

As far as the ATS playback "box" is concerned, the system can have the appropriate combination of computing capability that handles our requirements and is able to support an operating system other than Windows and has the appropriate working drivers to run multi-channel audio.

The system can be operational for streaming the individual audio files from the hard drive to the sound circuitry for D/A conversion. One embodiment encloses the Dolby AC3 audio decoder as it can help compress our file system immensely with no loss of fidelity, and it is in the public domain which will help to lower the price tag. However, due to the size of hard drives these days, one may be able to just put the whole ambience catalog on one hard drive in their original uncompressed native 48 k PCM format and still have space to spare These and other advantageous features of the present invention will be in part apparent and in part pointed out herein below.

BRIEF DESCRIPTION OF THE DRAWINGS

For a better understanding of the present invention, reference may be made to the accompanying drawings in which.

DETAILED DESCRIPTION OF INVENTION

Figure 1:
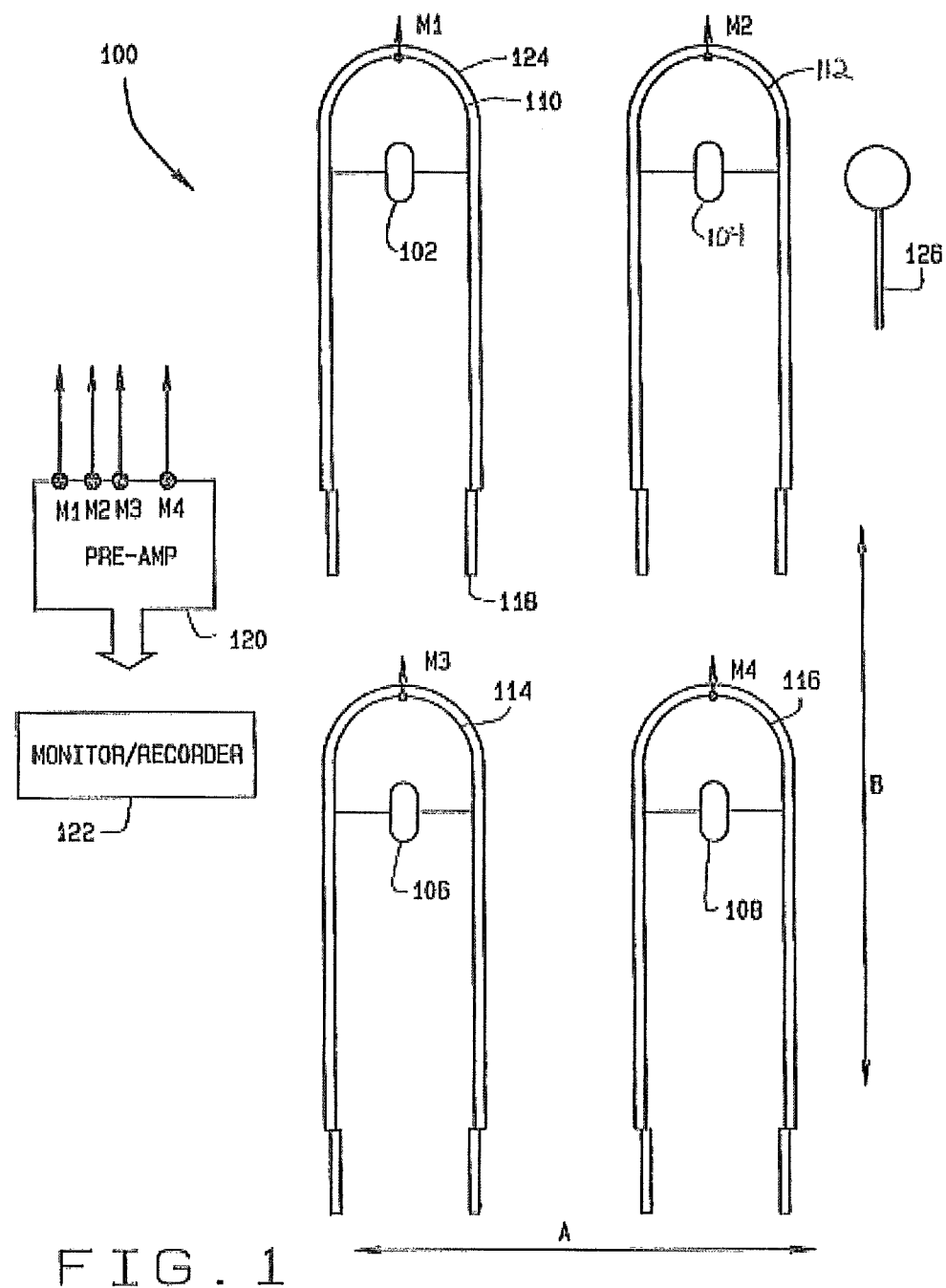
FIG. 1 is a basic schematic of a microphone array and recording device.

According to the embodiment(s) of the present invention, various views are illustrated in FIG. 1-9 and like reference numerals are being used consistently throughout to refer to like and corresponding parts of the invention for all of the various views and figures of the drawing. Also, please note that the first digit(s) of the reference number for a given item or part of the invention should correspond to the Fig. number in which the item or part is first identified. Also, various electronic equipment specifications are provided to illustrate examples of performance and operating specifications in the desired range for the present invention.

One embodiment of the present invention comprises a method of recording natural sounds at sound recording location with a matched microphone array, recording the signal on a high resolution recording device including creating an audio bed, and playing back the recording on a tuned playback system at a separate playback location teaches a novel apparatus and method for ambient therapy.

The details of the invention and various embodiments can be better understood by referring to the figures of the drawing and the various electronic equipment specification examples included herein by reference. Referring to FIG. 1, a representation of one embodiment of a microphone matrix array and recording system 100 is shown. The preferred embodiment shown in FIG. 1 is about approximately a 200'×200' array where four (4) 102, 104, 106 and 108 microphones are each placed at one of the four (4) corners of the 200'×200' space where Dimension A is about approximately 200' and Dimension B is about approximately 200'. The dimension of the array can be adjusted to better accommodate a given natural environment, however, the about approximately 200'×200' array is preferred in many natural environments, for example the woods or forest. The independent microphones will record sounds with a built-in time delay between microphones for each sound event as defined by the 200'×200' array.

Items 110, 112, 114, and 116 are a representation of a customized cage further ring in which the microphones are suspended in a bell and clapper configuration. The case, or covering, keeps moisture and debris off the microphone. The cages can be mounted on porcelain insulators 118. The microphones output signals M1, M2, M3, and M4 responsive to surrounding sounds and representative thereof. The signals are received into a pre-amp 120 and then monitored and recorded by the monitor/recording system 122. There is also preferably a rod 126 placed a proximate distance from the array for attracting away static. The rod is preferably about approximately 7 ft. in height above ground and is to be placed about 3-4 ft. away from array and preferably made of copper. The gauge and material of the microphone transmission lines may vary but is preferably selected to minimize signal noise and interference. The wind screen 124 is also represented which shields the microphone from the wind.

Figure 2:
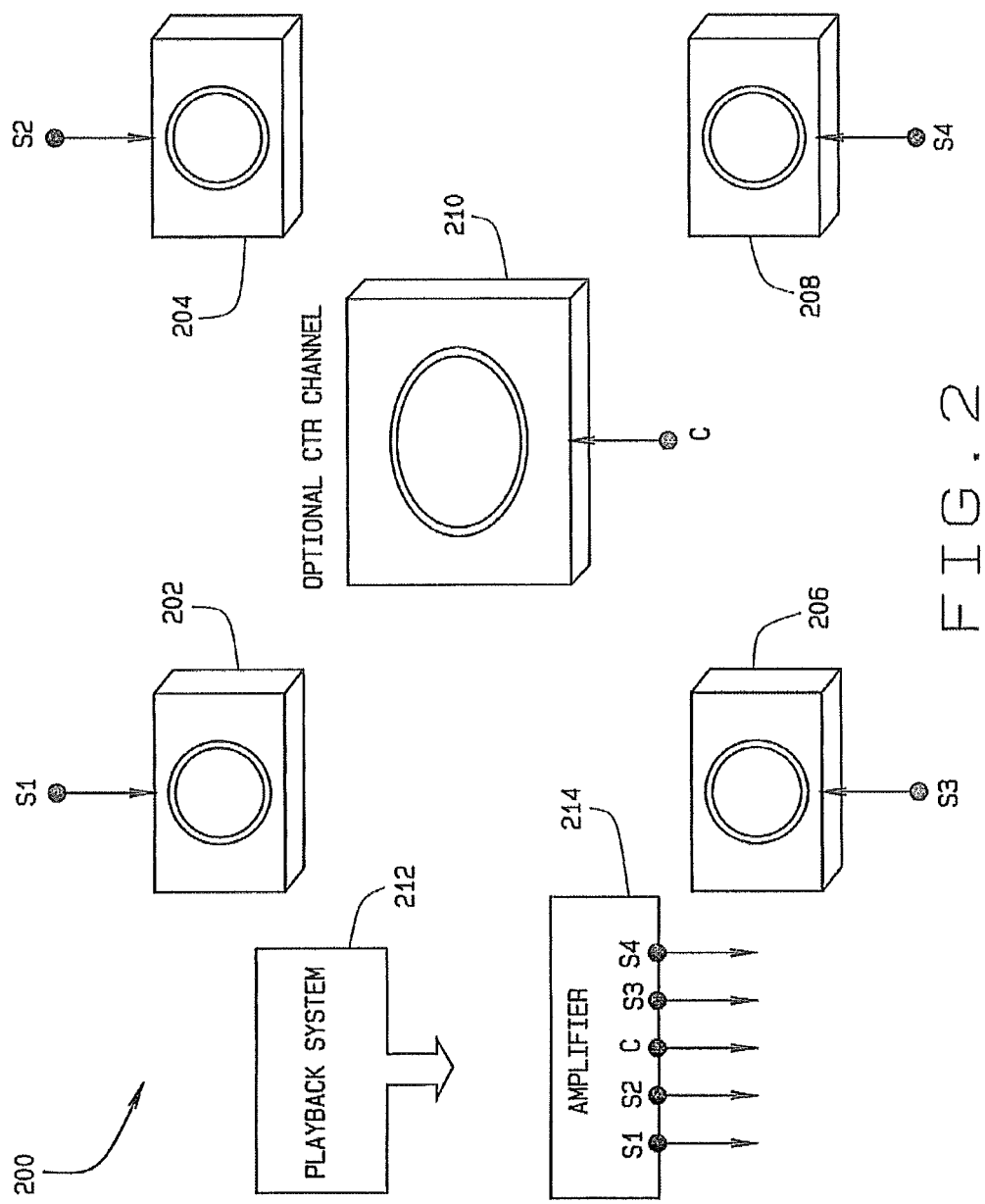
FIG. 2 is a basic schematic of a play back system.
Figure 3:
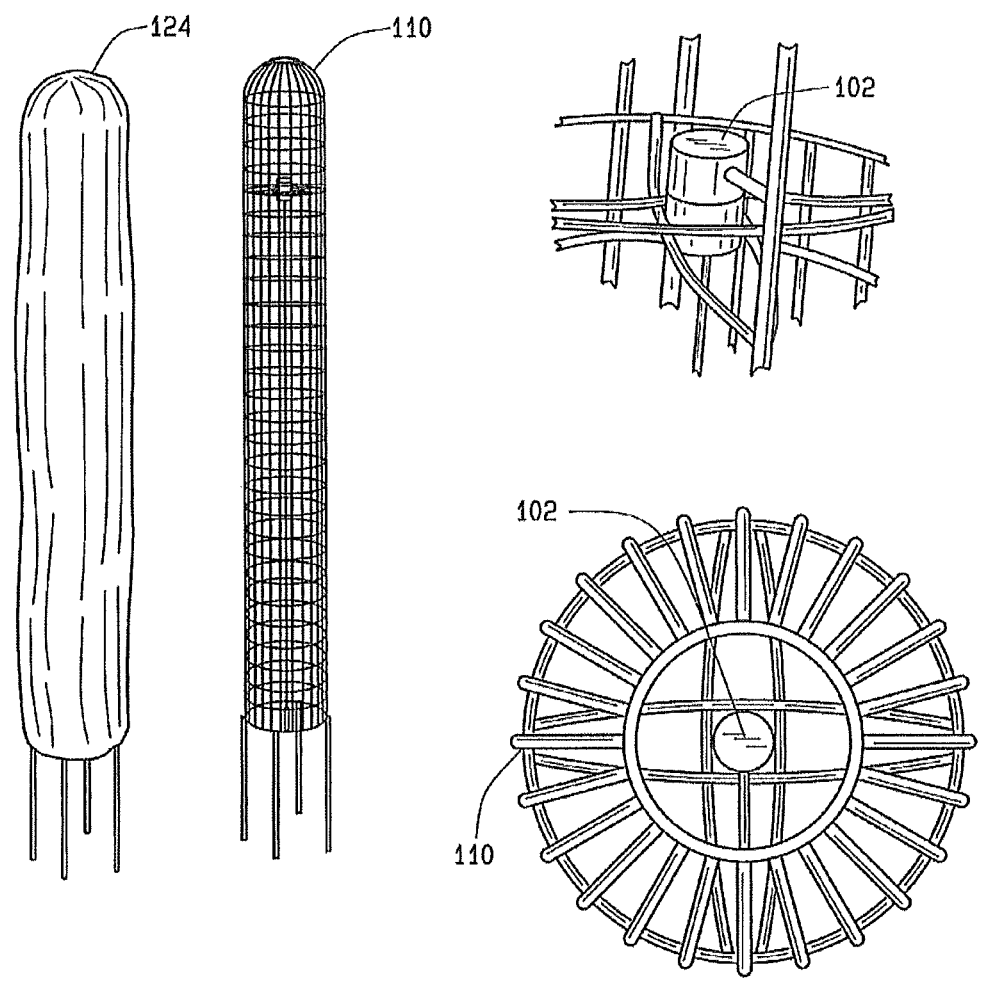
FIG. 3 is a perspective view of the microphone protective cage.

Referring to FIG. 2, a representation of a tuned and match speaker array and playback system 200 designed to maximize the ambient therapy effect is shown. There are shown four (4) matched speakers 202, 204, 206, and 208 and an optional center channel subwoofer 210. The playback system 212 plays back the signal through Amplifier 214, which generates signals $S_1$, $S_2$, $S_3$, $S_4$ and C. The center channel can be optional as indicated.

Ambient therapy is made of 2 major components.
1. recorded audio software
2. specific playback or delivery system The recording process is done in a microphone configuration which is referred to herein as the "4.1" technique. That means that the play back of the audio goes to 4 matched speakers and optionally 1 sub woofer. Natural sounds of the 4 seasons and other natural sounds such as waves can be recorded in this manner with microphone placement being 200'×200' with 200' between all 4 microphones. The playback system can include four (4) speakers for four (4) channel playback of sound each corresponding to the sound captured by each of the four (4) microphone channels and the playback system can alternatively include a subwoofer or center channel for playback enhancement of low frequency sound. This is referred to as the "4.1" technique. However, a "4.0" technique playback system can also be utilized, which does not include a subwoofer channel. The 4.0 or 4.1 technique can be alternatively selected to best satisfy a specific playback installation.

Once the season or ambient natural sound space is recorded, comprising several continuous, or sequential, or random hours of recorded material, the audio "bed" is reviewed, compressed and edited. Months of recording can be assembled into a 1 hr. format for delivery of the ambient therapy.

The microphones used preferably have a specification that includes a wide range of audible sounds and are omni directional. For example, there are two different brands of microphones that have the desired specification. One brand that can be utilized in the set up is Shure brand electret condenser MX 183 type microphones, which may have permanent installation, since they have proven to be more robust in a variety of weather conditions. Also, DPA brand 4060 electret condenser microphones can be utilized. Other microphones having similar performance specifications can be utilized The microphone pick up pattern can be "omni-directional" or "omni". The microphones pickup sounds from all directions. They are small "lavalier" type microphones. The microphones receive a wide variety of audible sounds of the location where they are placed. The microphone converts the audio sound energy to electrical signals that are transmitted (via hard wire, wireless transmitter, fiber optics and, etc.) to a microphone preamplifier. The amplified electrical signal from each microphone is then manipulated in a number of ways:
1.) converted to an audio signal for monitoring purposes
2.) modified electronically for content i.e.—low frequency interference, hum removal, etc.
3.) converted to a digital signal for storage on an appropriate high resolution medium (tape, disc, etc.)

These 4 microphone signals are electrically transmitted by shielded cable under ground to a multi-channel, high resolution digital audio recorder as a storage medium for the raw audio. The microphone mounts consist of:
1.) a custom designed wind screen coated with a waterproof fabric to weather protect the microphones and reduce the amount of objectionable wind noise picked up by the microphones.
2.) a custom designed "cage" manufactured to suspend the microphones upside down in a bell and clapper configuration in order to keep moisture from conflicting with the purity of the signal.
3.) the cage can be, in turn, mounted on porcelain insulators.

A 7 foot solid copper rod can be placed in the ground about approximately 3-4 feet away in order to attract any static charge that may conflict with the purity of the signal. The microphone transmission cable is of an appropriate gauge multi pair wire, in a shield to block rf interference. The transmission cable can run 1000' to the microphone preamps, then to the monitoring system and a high resolution multi channel digital audio recorder, which is a 24 bit, 48 khz digital resolution. All 4 channels can be recorded simultaneously.

Once the raw audio is recorded, the time compression takes place to create the audio "bed". The digital audio is transferred from the digital audio tapes to a computer based audio recording, editing, and playback system for greater flexibility. Then, music is custom designed to integrate at specific times on the audio bed based on events triggered by nature sounds that occur in the ambient sound space. Custom sound effects may also be created and included to enhance or augment the natural sounds or music content.

The content of the music can be guided and customized for the purpose of the specific intention of each therapy, for example pain distraction, or child birth. This is an important component because it addresses the creative process of the composer being inspired by the natural sounds as it relates to a purpose driven objective. The natural sound events are used as a key or trigger to guide the musical overlay in a manner to achieve the desired target therapeutic effect.

The present method and system is not the creation of music for music sake, or sounds for sounds sake, rather, a creative process applied to generate and create a specific outcome that has to do with healing, therapy, etc.

The delivery system hardware is made up of:
1.) a playback unit system
2.) specific code wire
3.) a shielded speaker system
4.) an amplification system Another hardware component is the installation and tuning of the Ambient Therapy listening room so that the patient receives the greatest benefit from this modality of treatment. The concept and use of the treatment can be used for:
1.) pain distraction
2.) anxiety distraction
3.) transient spike masking for unwanted sounds surrounding the Ambient Therapy rooms "hospital sounds" etc.

One theory is that this distraction, is due to the evolution of the Human auditory system where sound, has the ability to address the auditory nerve and suspend belief as to the location of the individual and may cause various effects like day dreaming.

One key feature of the preferred embodiment goes back to the 200'×200' algorithm or array created at the time of the recorded "bed". The listener/patient can be allowed to mentally place themselves "in a 3 dimensional acoustic space" because of the present technique. If content were presented in a single (mono), or stereo (two channel) method, the present unique 3 dimensional surround component would not be present. The therapy results would likely not be the same if not presented in surround 4.0, or 4.1.

The musical content addresses the emotional make up, more specifically. The recording process, in conjunction with hi end equipment in a 200'×200' configuration, musical content specifically designed, and a delivery system as a control for the output of the material are all critical to the method.

The playback system configuration can take on various embodiments having various performance specifications without departing from the scope of the present invention. Listed below are three possible embodiments having varying performance specifications.

First Embodiment
Computing Platform
Motherboard: VIA EPIA M Mini-ITX motherboard
Processor: VIA C3/EDEN EBGA Processor 600 MHz Fanless
Memory: 512 MB SDRAM DDR-266
Audio Processor: VIA VT1616 6 channel AC'97 Codec
Storage
Hard Drive: 160 GB Western Digital Caviar, 7200 RPM, 8M cache
Optical Storage: 16X DVD ROM
Software
Operating System: Microsoft Windows XP Professional was chosen for its 6-channel audio support and development tools.
Programming Language: Microsoft Visual Basic was used to simulate the front panel display and controls in software to emulate the physical panel.
Audio File Format: Extensible Wave was utilized as it is the default Windows format
User Interface
Front Panel: The Crystalfontz 633 front panel LCD & keypad was chosen for its two line LCD display, the 6 button keypad, and its ability to fit into a drive bay.
Analog Audio Section
Power Amplifier: 4 discrete channels −50 W/4Ω custom class D audio power amplifiers
Power Supply
CPU Power: ITX-PB 200 W Internal ITX Power Supply
Audio Power: Astrodyne SPU130-108 130 W 24 V Universal 85-265VAC Input
System Case
ATS Case: ITX-PB ITX Checker Cube Case
Speaker System
Speakers: Speco Technologies SP-6MA/T 6.5" ceiling mount coaxial speaker Second Embodiment
Computing Platform
Motherboard: VIA EPIA MS Mini-ITX
Processor: VIA C3/EDEN EBGA Processor Fanless
Memory: 512 MB SDRAM DDR-266
Audio Processor: VIA VT1616 6 channel AC'97 Codec
Storage
Hard Drive: IBM/Hitachi 2.5" 8 MB cache Enhanced 24/7 usage
Optical Storage: Panasonic Slot Load DVD ROM
Software
Operating System: Microsoft Windows XP Professional was chosen for its 6-channel audio support and development tools. Also, preliminary Linux migration and experimentation.
Programming Language: Microsoft Visual Basic is being used to simulate the front panel display and controls in software to emulate the physical panels and test out new features as they are requested.
Audio File Format: Dolby AC3 multichannel format and investigation of possible encryption scenarios to assist in copy protection.
User Interface
Front Panel: Custom designed pushbutton key matrix, volume control and trim controls
Display: Noritake dot-matrix vacuum fluorescent display
Analog Audio Section
Analog Level and Trim: Custom designed VCA driven preamp, 4 channels with main and trim controls
Power Amplifier: Custom designed 4 channel −50 W/4Ω custom class D audio power amplifiers
Power Supply
CPU Power: ITX-PB 200 W Internal ITX Power Supply
Audio Power: Custom designed multiple output DC supply
System Case
ATS Case: Various cases are being evaluated
Remote Control
Remote Control: Implementation of a wireless system emulated through software
Speaker System
Speakers: Further experimentation and evaluation of different speakers including the Speco Technologies SP-6 MA/T 6.5" ceiling mount coaxial speaker Third Embodiment
Computing Platform
Motherboard: Cost effective solution that passes all quality and life testing
Processor: Fanless processor that accompanies the chosen motherboard
Memory: Adequate memory to handle all system functions
Audio Processor: Audio codec selected with the chosen motherboard
Storage
Hard Drive: IBM/Hitachi 2.5" 8 MB cache Enhanced 24/7 usage
Optical Storage: Panasonic Slot Load DVD ROM
Software
Operating System: A royalty free Linux OS custom configured for this application.
Programming Language: The C programming language under Linux.
Audio File Format: Dolby AC3 multichannel format and investigation of possible encryption scenarios to assist in copy protection.
User Interface
Front Panel: Custom designed pushbutton key matrix, volume control and trim controls
Display: Noritake dot-matrix vacuum fluorescent display
Analog Audio section
Analog Level and Trim: Custom designed VCA driven preamp
Power Amplifier: Custom designed 4 channel −50 W/4Ω custom class D audio power amplifiers Power Supply
  CPU Power: ITX-PB 200 W Internal ITX Power Supply
  Audio Power: Custom designed multiple output DC supply
System Case
  ATS Case: A custom case that meets the required feature needs and visual styling desires.
Remote Control
  Remote Control: Implementation of the physical counterpart from the emulated system tested through software
Speaker System
Speakers: Full range ceiling mount coaxial speaker that is magnetically shielded The above embodiments are merely illustrative examples of how the system can be implemented. However, the specific components may vary without departing from the scope of the invention.

Figure 4:
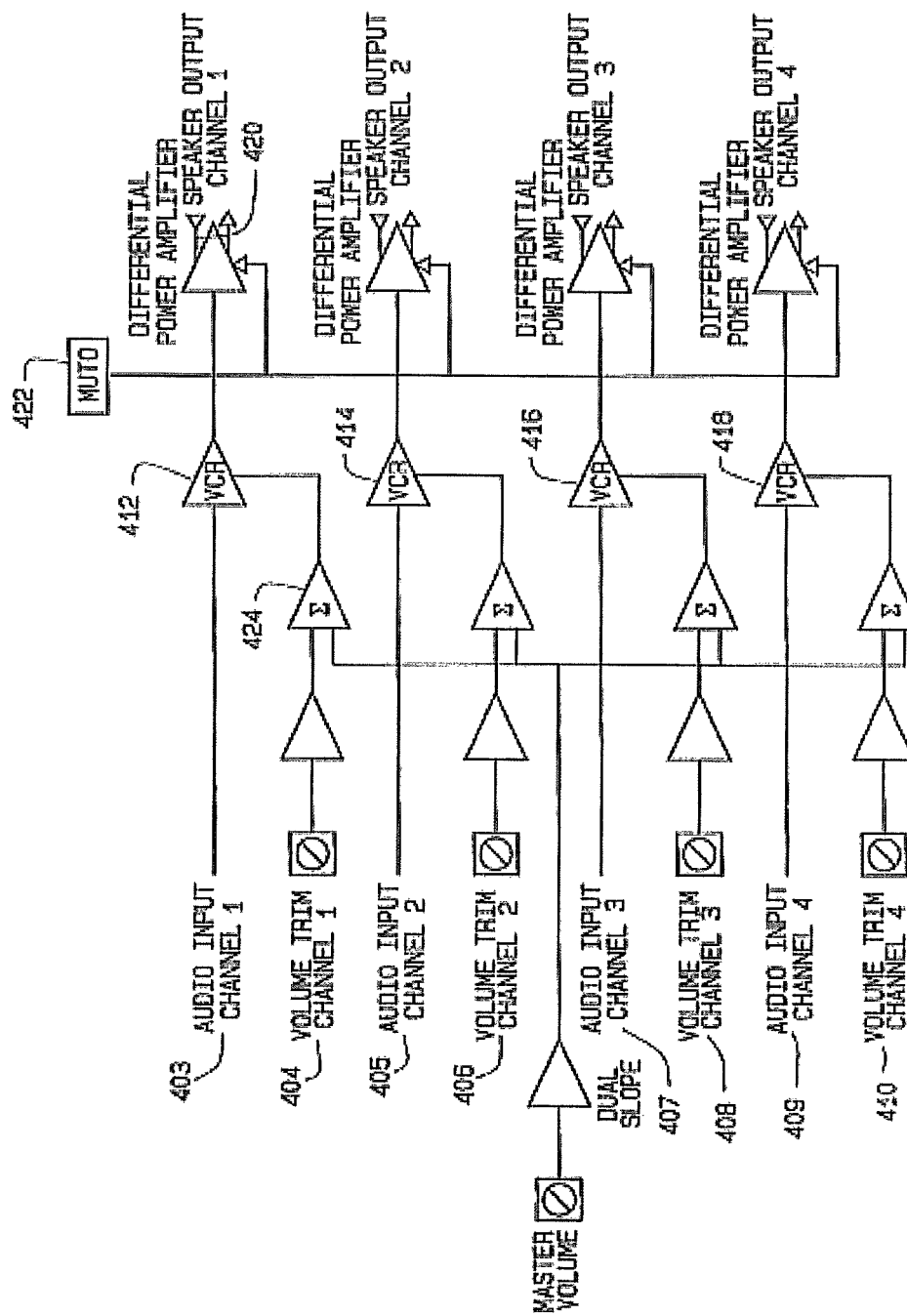
FIG. 4 is a block diagram of the ATS Analog Board.

Referring to FIG. 4, the ATS analog board's primary function is to take the low level analog audio output signals from the ATS's CPU motherboard and provide adequate amplification to those signals in order to drive an array of loudspeakers. The design for the Voltage Controlled Amplifier (VCA) based preamplifier design can include one master control and individual trim controls 404, 406, 408, 410 for each channel 403, 405, 407, 409. The ATS is a multichannel audio output device. This means that there are multiple discrete channels of audio running simultaneously that need to be controlled simultaneously in some reasonable fashion. One embodiment of the ATS analog board is described in detail below, however, the analog board design can vary without departing from the scope of the present invention.

The traditional approach is to utilize a stacked potentiometer style volume control, essentially four volume controls sandwiched together and operated from a single mechanical rotation. This approach is low tech, but very reliable. However, there are shortcomings. The first and foremost is the fact that the individual channels cannot be trimmed slightly as all the pots are bonded together. With the ATS, it is necessary to control all four channels simultaneously, but also have the ability to trim each channel unique to accommodate potential mismatches in the placement of the speakers in the end installations. Therefore, with the above criteria, the analog board was designed using a voltage controlled amplifier. Essentially, the VCA is a sort of supervisory potentiometer that will change the gain through it via a simple direct current control voltage. By constructing each channel identically with a VCA preamplifier 412, 414, 416, 418, each channel can be linked together and driven from one central control source as well as being individually trimmed.

The efficient audio power amplification for driving typical low impedance loudspeakers can be implemented because the ATS would be located in sometimes small and compact equipment shelves or closets, it was necessary to adopt a design topography for the power amplifier that would be reasonably efficient and not generate excessive heat. The power amplifier section in the ATS is what is termed a switching power amplifier or class D style amplifier 420. In conventional audio power amplifiers, much of the inefficiencies are consumed by having a certain amount of the available electrical current turned to heat in the output devices of the amplifier instead of actually being transferred to the speaker load. Due to the nature of attempting to control current to a load in a linear fashion, this particular effect is unavoidable. What a switching power amplifier does is to waste very minimal amount of current that is consumed by the power amplifier's internal output devices and send nearly all of the current to the load. This is accomplished by simply not allowing the output devices to have a linear response, but more of a discrete and binary response. Either the output devices are fully on and conducting or they are off and not conducting current to the load.

The ATS play back system implements a master mute control, which governs all channels simultaneously. As part of the analog board's functions, a master mute 422 control can be incorporated to facilitate the need to abruptly mute the audio should there be a reason for the end user to do so. This function is simply enabled by depressing a pushbutton which will toggle the audio amplifier into a state of mute. With another subsequent press of the button, the mute circuitry will be disengaged and the audio amplifier will function normally.

The analog board can be designed with flexible topography for the inclusion of a software controlled volume control for recalling preset level scenarios and remote control implementation. With incorporating a VCA based preamplifier, the ATS is capable of being upgraded to become software controlled. This allows for future implementation of software controlled volume functions including preset volume levels for recalling in specific scenarios. As well, a wireless remote control can be added to the system with relative ease without redesigning the entire preamplifier circuitry.

The audio signal from the CPU motherboard is transmitted to the ATS analog board and when the audio signal is received by the ATS analog board it is input to the VCA amplifier. This can be seen in FIG. 4. The audio signal's exiting current level from the VCA or gain through the amplifier is controlled by a linear DC control voltage, which then corresponds to an overall logarithmic throughput from the VCA. There are two sources of control voltage for each channel's VCA on the ATS's analog board. These sources can be seen in FIG. 4.

The #1 source of control voltage can be from the main volume control. This can include a single potentiometer that generates a control voltage based upon where the position of the volume control is located. It can be arranged so that clockwise rotation will produce a positive gain through the VCA. This particular control voltage amplifier can also be configured to give a dual slope response. When the unit is operated at low levels, the volume control will effect a larger range of gain. The control can be designed such that at about 1 o'clock on the volume control, the slope of the gain decreases and so a larger movement on the control produces a much smaller shift in gain. This can help alleviate a possible accident if a person should rotate the control too high too quickly.

The #2 source of control voltage is from an individual trim control. The interface to this control can be situated on the rear of the ATS unit and can allow the system installer to adjust the individual gains on the channels of the ATS to accommodate possible differences in the speaker volumes at the listening position because of possible obstructions in the room or few choices with which to install the speakers. This control is simply a linear control that can span roughly over about a 30 dB range, +/−15 db of gain or attenuation. The two control voltage sources can then be summed 424 to produce a single control voltage which is fed into the VCA. Each channel has its own unique trim control and summing with the main volume control voltage to produce a unique control voltage for each channel. After the audio current exits the VCA section, it is then fed directly into the power amplification section. See FIG. 4 for a view of the power amplifier section.

The output of VCA can be injected into the power amplifier section. The power amplifier can be based on a class D style pulse width modulating scenario. The incoming audio can be modulated with a high frequency triangle waveform and a pulse width modulated output can be fed into a series of transistors controlling the current delivered to the speaker load. The output scenario is what's termed a differential or balanced bridge output. This means that there is no solid ground reference with a single-ended fluctuating output. But instead, there are symmetrically opposite signals that are opposite in phase and act as a sort of push-pull on the speaker load. This allows the amplifier to produce a net voltage output across the load that is nearly double what can be achieved alone by running the amplifier in a single ended mode.

The power amplifier can have shutdown protection circuitry embedded into the design that will shut the amplifier down in case of a fault in the speaker load or over exertion of the amplifier. Also included, can be circuitry that will effectively shut the power amplifier down amounting to a mute function. This function can be embedded into the amplifier section directly with discrete circuitry instead of being software controlled in the program that runs the ATS. The mute circuit can toggle its state from the input from the user on a pushbutton switch. A single button push will shut down all four amplifiers on the analog board. The state will stay latched until the user again depresses the pushbutton and the mute circuit will reactivate the amplifiers.

All of the functions described above for the ATS analog board function together harmoniously as a whole to produce a single board, four channel preamplifier/power amplifier solution specific to the requirements of the ATS player. The specific details of the design of the board may vary without departing from the scope of the present invention.

Figure 5:
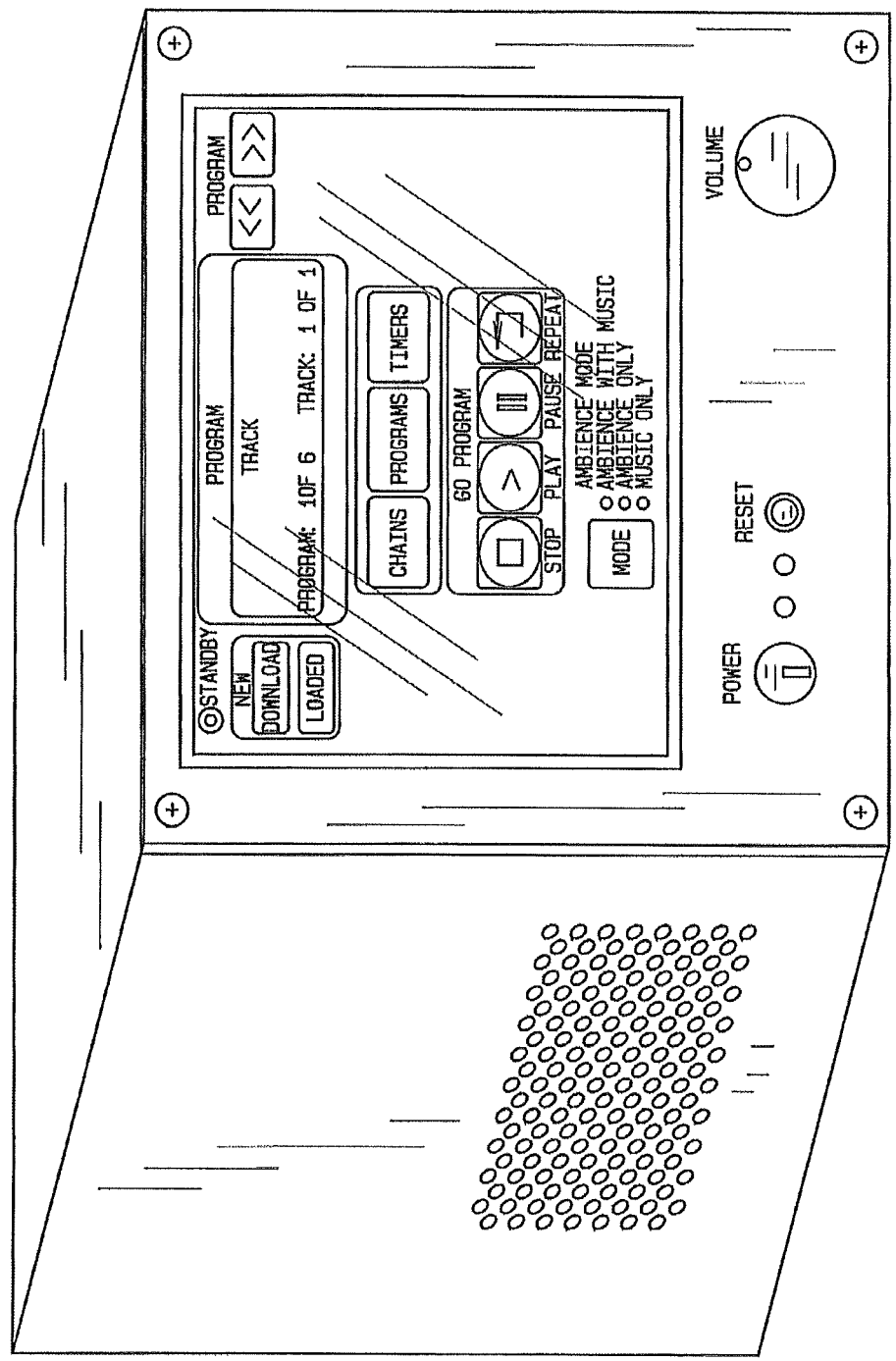
FIG. 5-9 are various user interface screens.
Figure 6:
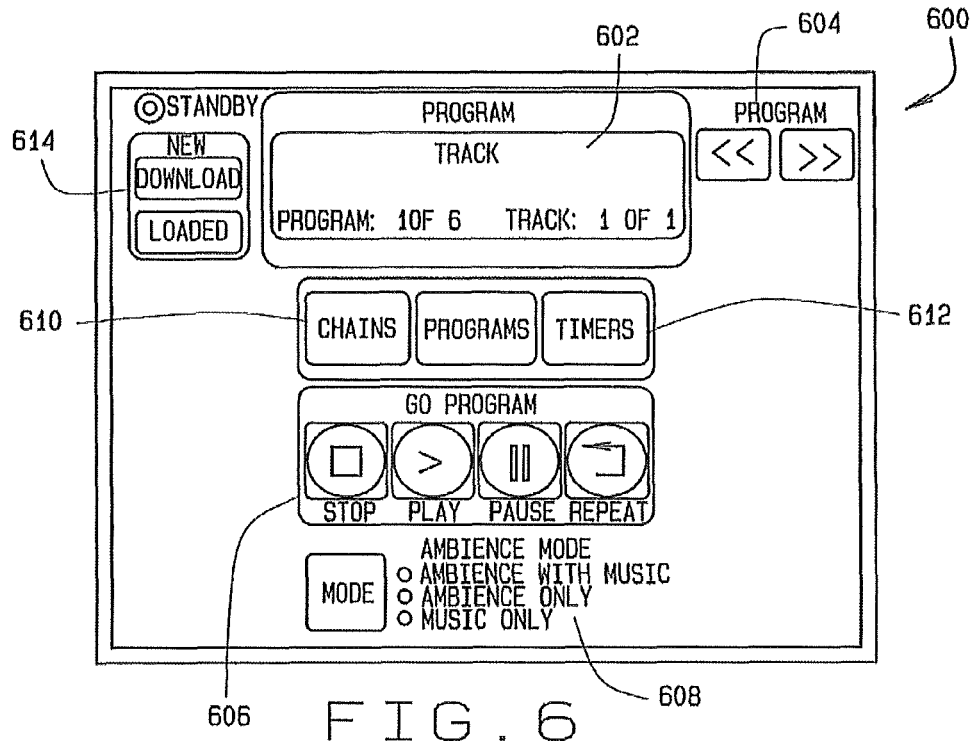

The user interface of the present invention can include an LCD touch screen monitor, refer to FIG. 5, and display driver where the user interface screen presentations are provided by the ATS software user interface application. Software applications for generating such user interfaces is well known to those skilled in the art. The user interface application can be operable to implement various features including the following features.

Referring to FIG. 6-9, many of the user interface screens including the main menu interface screen 600 includes a program display window 602 that displays the title of the program and track being played, the program and track identification numbers. Program and Track Forward and Backward Skip Button 604 and, are also provided on the main menu, which allows the user to skip forward to the next program or track or skip backward to the previous program or track. STOP-GO-PAUSE-REPEAT buttons are also provided 606. The repeat function when selected repeats the current program or track being played. Three ambience modes 608 are provided, as there are 3 ways to listen to any ambience title and they are—1.) ambience with music; 2.) ambience only; 3.) music only. The ambience refers to natural sounds recorded.

The main menu also provides a push button for selecting Chain programming 610. The Chain programming option refers to "chaining" one program to another, refer to FIGS. 8-9. This can be done with any of the 3 ambience mode functions. An example of a chain is NIGHT SONG/Ambience Only chain to SUMMER SONG/Music Only chain to BIRD SONG/Ambience and Music. A program corresponds to an ambience title, which includes ambience with music, ambience only and music only. Programs refer to the programs or titles loaded in memory. When a program is selected for play, the names show up in main program display window, top-center. In order to search for and find a program, the Forward and Backward "Skip" < > buttons on program function next to the window can be utilized to page through the list of programs available. The Prey and Next Track buttons allow you to page through tracks in a program were a track refers to the subfile of recording segment within a program or title.

Figure 7:
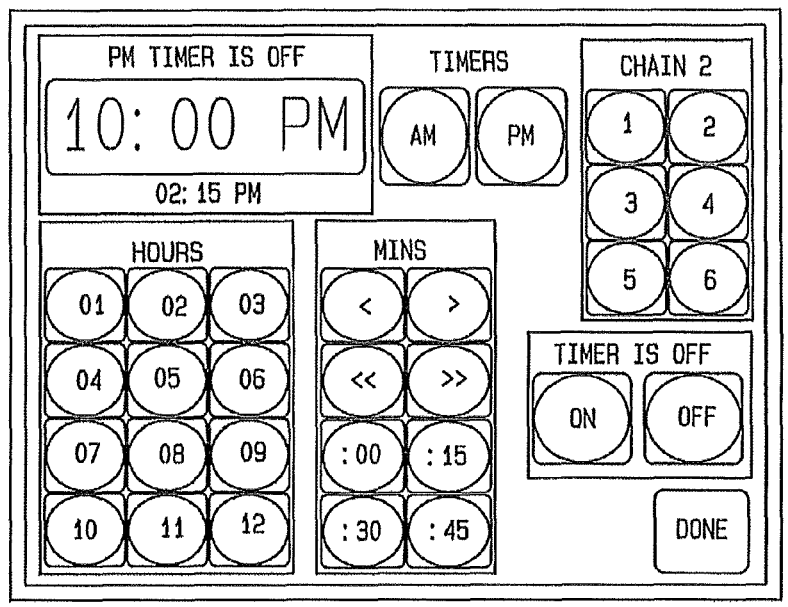
Figure 8:
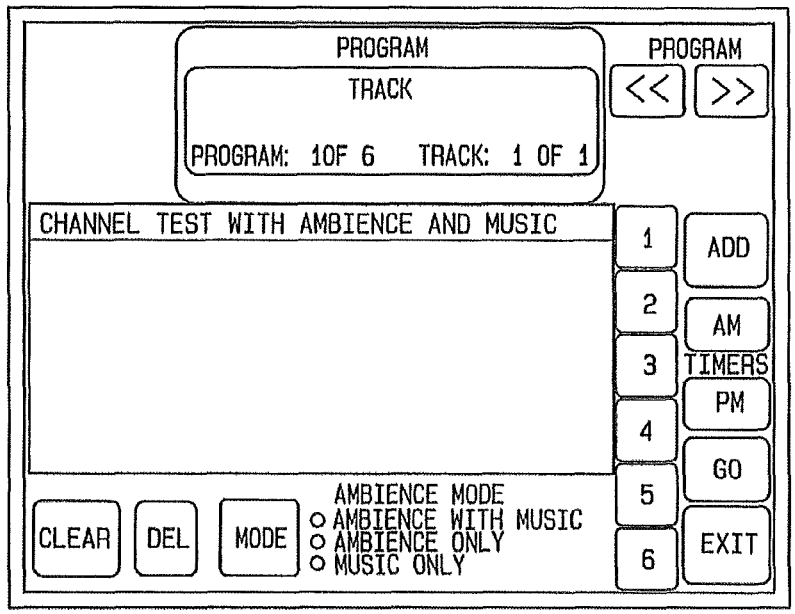
Figure 9:
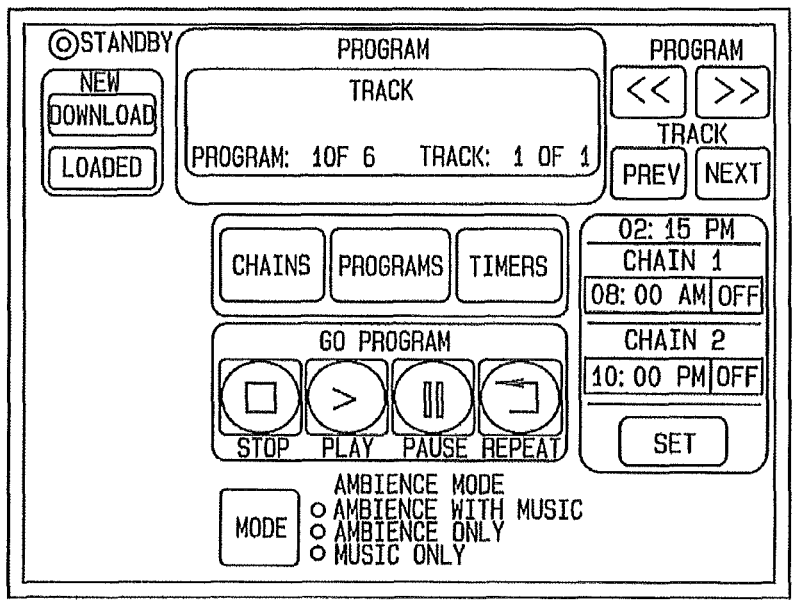

The main menu also provides a Timers button 612 for selecting the timer option, refer to FIG. 7. The timer function is an alarm clock type function for setting start times for programs. The purpose of the timer function is to auto start a chosen program. This capability can be used for "biorhythm reset" in an individual when losing track of day-night. The timer function allows the user to select a preset start time for a given program or chain, where the program or chain is appropriate for the start time selected.

The New Download indicator 614 can allow the user know when ethernet down loads are available. When the Down Load indicator light is flashing, it indicates that a new program is available to download. The ambient therapy playback system can access new programs via a communication port or network to a wide area network or local area network. In order to access and load, the user simply presses the flashing download button. When the download is complete, the "Loaded" button will flash to indicate that it has been successfully downloaded to the playback system. The Loaded button can be adapted to flash for 2 weeks to indicate download in case of staff changes during load function.

An example of the applicability of the ATS playback system is its use in a hospital environment for pain distraction. For example the user has a patient that has pain from hip surgery. In this excruciating state, some medical research has shown that the patient can feel trapped in their thoughts and mind. It apparently can be difficult or nearly impossible to escape such feelings. A distraction can be achieved by playing "SUMMER SONG" Ambience and Music to place the patient in a summer thunder storm. The concept is that humans hear this music in a couple of levels. The natural sounds such as for example thunder, rain drops striking hard surfaces, and wind can create an evolutionary awareness of exactly where we might be, and as the music portions begin, that part addresses a more "executive" function of the brain. The music overlay is composed by using the natural sound events as a guide or trigger such that the music naturally flows with the natural sounds without over shadowing the natural sounds. The concept is that pain signals move slower than auditory signals, so in theory, the "ear-gate" function of the body can distract the individual from one signal to another. The compression and editing of several hours of natural sound into a more brief format such as for example a one-hour format floods the human ear gate with a sound bed that dominates and distracts the mind of the listener. Thus, one month of sound recordings in a wooded forest area can be edited to a 1-hour format saturated with autumn sound events such as for example blowing leaves across and over a grassy area the sound events can be utilized as a trigger for the customly composed musical overlays.

To program a selection the user can go to main screen program and choose a program, for example AUTUMN SONG with the arrow keys to right of the program display window. The user can utilize the "mode" button and select Ambience With Music and hit play. If the user chooses to extend the experience, the user can do several things: 1.) simply hit the repeat button and it will repeat the program until the user manually hits stop; 2.) "chain" this program to another version of the program i.e.: music only, or ambience only, or chain it to an entirely different program (bird song for example). To create a chain, the user will select the chain button at which time the chain set-up screen will appear with AUTUMN SONG displayed in the program display window and designated as chain 1 of x. to add AUTUMN SONG as the first link in the chain select add, and repeat this for every program link in the chain; 3.) once the chain sequence has been input, if the user wants this "chain" to start at a specific time, the user can select the "timers" function. The prompt to the right of the main function buttons has "set". The program start can be set just like an alarm clock.

set
    main timer window opens
    select am or pm
    chose the hour and min.
    push on and
    done
    to deactivate this function, chose off. this can be done on
        big "set" window, or on main screen in timer window (off-on to the right side) red is a function of "stop".

1. there are 2 timers. am and pm. a timer function is a function of "go" so it is green. (green light go).
2. there are 6 chains possible with 2 timers possible per chain, so in total: 12 timers possible.

Another example is a scenario were the patient is delusionary with loss of awareness of day-night. The user can try to reset the patients biorhythm by using the timer function in conjunction with a specific program sequence:

1. chose bird song ambience only
    add to chain then
    chain to bird song ambience with music
    activate timer and set for (7 am).
    press on
    done
    the purpose here is that in our duality of hearing, we are slowly waking the patient with the sound of morning birds in our evolutionary hearing . . . then adding higher "executive function" hearing with the addition of the music. this sequence can be approx. 2 hrs. and ramps up
2. choose night song "ambience with music".
    add to chain
    chain night song ambience with music to night song ambience only.
    activate timer and set for (10 pm)
    press on
    done The purpose here is to slow down activity in a similar manner as the am sequence.

The various method and system ambient therapy examples shown above illustrate a novel concept for ambient therapy. A user of the present invention may choose any of the above ambient therapy embodiments, or an equivalent thereof, depending upon the desired application. In this regard, it is recognized that various forms of the subject ambient therapy method and system could be utilized without departing from the spirit and scope of the present invention.

As is evident from the foregoing description, certain aspects of the present invention are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the sprit and scope of the present invention.

Other aspects, objects and advantages of the present invention can be obtained from a study of the drawings, the disclosure, the example specifications and the appended claims.

What is claimed is:

1. An ambient therapy recording and playback system comprising:
   a rectangular array of microphones comprising four independent multi-directional matched microphones and each of said matched microphones are independent of any other microphone and positioned symmetrically about a center point of the rectangular array and each microphone positioned at one of the four corners of the array thereby having an established sound pickup time delay between matched microphones; and
   a recording system having four independent recording channels where each channel receives an independent microphone signal from one of the independent matched microphones independent of any other microphone signal for receiving sounds independently captured by each matched microphone, and further having an electronic storage having stored an electronic recording of each channel's captured sounds thereby having an established recording as an audio sound bed,
   where the matched microphones are positioned in a 200 ft. by 200 ft. rectangular array,
   where the audio sound bed contains a naturally occurring transient audio event, and
   where the recording system has a musical composition stored and has a musical overlay function that overlays the naturally occurring transient audio event with a matching musically composed audio event from the musical composition establishing an audio program.

2. The ambient therapy recording and playback system as recited in claim 1, comprising an ambient therapy playback system having an audio output projecting the audio program audibly.

3. The ambient therapy system as recited in claim 2, where the playback system is a four channel ambient therapy playback system including electronic storage for storing the program and a four channel amplifier with four outputs configured to drive four speakers for playback of the audio program.

4. The ambient therapy system as recited in claim 2, where the playback system further comprises a user interface for controlling the ambient therapy system.

5. The ambient therapy system as recited in claim 4, where the playback system has a network interface having a download function that downloads one or more of audio programs and software.

6. A method for recording and playing back therapeutic audio comprising the steps of:
   capturing natural sounds with a rectangular array of matched microphones and said matched microphones comprising four independent multi-directional microphones arranged symmetrically about a center point of the rectangular array where each microphone is independent of any other microphone and each positioned at one of the four corners of the array establishing a sound pickup time delay between matched microphones;
   outputting four independent signals, one from each of the four microphones, where said signals are representative of the natural sounds captured;
   receiving and recording the four independent signals simultaneously each independent of any other microphone signal with an independent four channel recording device creating a four channel audio sound bed comprising naturally occurring transient audio events;

composing a musical composition comprising matching musically composed audio events where the content of the musical composition and the inclusion of the matching musically composed audio events of the musical composition is based on the naturally occurring transient audio sound events in the audio sound bed;

overlaying the musical composition over the recorded audio sound bed and matching the matching musically composed audio events with the naturally occurring transient audio events.

7. The method for recording and playback as recited in claim 6, where the rectangular array of microphones is a 200' × 200' square array and where the microphones are omni-directional microphones.

8. The method of recording and playback as recited in claim 7, further comprising the steps of:

providing a protective cage as the support frame surrounding the microphone and a windshield over the cage.

9. The method for recording and playback as recited in claim 7, further comprising the step of:

providing a static attracting rod spaced proximately adjacent outside the array.

* * * * *